United States Patent
Romey et al.

(10) Patent No.: US 6,846,678 B2
(45) Date of Patent: Jan. 25, 2005

(54) GAMMA STERILIZED BUFFER SOLUTIONS FOR PH MEASUREMENT

(75) Inventors: Matthew Romey, Long Beach, CA (US); Mark Takagi, Orange, CA (US)

(73) Assignee: Terumo Cardiovascular Systems, Co.-Tustin, Tustin, CA (US)

(*) Notice: Subject to any disclaimer, the term of this patent is extended or adjusted under 35 U.S.C. 154(b) by 0 days.

(21) Appl. No.: 10/720,255

(22) Filed: Nov. 25, 2003

(65) Prior Publication Data

US 2004/0121469 A1 Jun. 24, 2004

Related U.S. Application Data

(60) Provisional application No. 60/434,816, filed on Dec. 20, 2002.

(51) Int. Cl.[7] ............................................... G01N 31/00
(52) U.S. Cl. .......................... 436/18; 436/8; 436/163; 252/408.1
(58) Field of Search .............................. 436/8, 18, 163, 436/174, 176; 252/408.1

(56) References Cited

U.S. PATENT DOCUMENTS

| 3,198,251 A | * | 8/1965 | Shore ........................ 424/76.7 |
| 4,370,314 A | * | 1/1983 | Gaffar ........................... 424/54 |
| 5,045,529 A | * | 9/1991 | Chiang .......................... 514/6 |
| 5,290,781 A | * | 3/1994 | Espino et al. ........... 514/266.22 |
| 5,308,849 A | * | 5/1994 | Miyazaki et al. ........... 514/279 |
| 5,397,704 A | * | 3/1995 | Boctor et al. .............. 435/214 |
| 5,438,060 A | * | 8/1995 | Miyazaki et al. ........ 514/262.1 |

FOREIGN PATENT DOCUMENTS

| GB | 1053615 | * | 1/1967 |
| JP | 7-258050 | * | 10/1995 |
| JP | 10-212220 | * | 8/1998 |

* cited by examiner

*Primary Examiner*—Maureen M. Wallenhorst
(74) *Attorney, Agent, or Firm*—Burns, Doane, Swecker & Mathis, L.L.P.

(57) ABSTRACT

The present invention provides storage stable, aseptic buffer solutions suitable for gamma sterilization. The buffer solutions include benzethonium chloride as a biocide, and avoid the acidification effects and the formation of precipitates that can be caused by gamma sterilization.

20 Claims, No Drawings

GAMMA STERILIZED BUFFER SOLUTIONS FOR PH MEASUREMENT

This application claims priority under 35 USC 119(e) to provisional U.S. application Ser. No. 60/434,816, filed on Dec. 20, 2002.

FIELD OF THE INVENTION

The invention pertains to buffer solutions formulated for calibrating pH electrodes. The buffer solutions are amenable to sterilization by gamma irradiation without resultant acidification, generation of significant quantities of $CO_2$, or precipitation of any components, excipients, or byproducts.

BACKGROUND OF THE INVENTION

Every pH electrode is an imperfect tool that functions unevenly over the whole pH range, and every pH reading involves a possibly variable liquid junction potential. Accordingly, it is necessary to have a standard or reference solution against which one can confirm the accuracy of a pH measurement system.

The National Bureau of Standards has identified a series of aqueous buffers that are commonly used to create solutions of specific pH values at specific temperatures. Weast, R. ed., CRC Handbook of Chemistry and Physics, (1979), p. D147–D149. The pH of the standards is temperature dependent, primarily because of the variation of the $K_a$ of the buffer system with temperature. The buffers comprise various active ingredients, e.g. phosphate, phthalate, borax, tartrate, etc. For measurements near neutral pH levels (6–8), the industry standard for pH electrode calibration solutions is a phosphate buffer.

Occasionally, however, pH measurements must be made in vivo, or in physiological environments or materials that must be isolated or protected from microorganisms and associated antigenic substances such as pyrogens. In such instances, additives such as biocides are introduced to inhibit microbial growth during processing, and a sterilization cycle is performed to ensure sterility of the finished formulation. Both measures can affect the pH of the standard solution.

The addition of preservatives such as biocides alters the physicochemical properties of the formulation and increases the potential for chemical interactions. Among other things, those new properties and interactions can alter the pH, and thereby render the solution ineffective for its intended purpose.

Likewise, the introduction of a sterilization cycle to ensure the sterility of the finished formulation can complicate the physicochemical profile of the sterilized product. Further, sterilization complicates the selection of a preservative since any such preservative must first be an effective biocide, but must also withstand the rigors of sterilization without affecting the pH, stability, cosmetics, or biocompatibility of the buffer. The preservative does not need to retain biocide effectivity post-sterilization, as long as it does not otherwise adversely affect the performance of the product.

Phosphate buffered solutions are preferred calibration buffers for neutral pH. However, phosphate buffers are excellent growth media for microorganisms. Even short periods between buffer manufacture and product sterilization can lead to bioburden levels high enough to threaten the integrity of a sterilization cycle. Conventional calibration buffers used for common laboratory pH electrodes often do not use preservatives. This is because the end application of such buffers is concerned solely with pH, and is not concerned with bioburden (which generally does not affect the pH of those well-buffered solutions). Medical device manufacturers, however, do not have this luxury. Systems and solutions used for the measurement of pH must often be aseptic. Thus, there is a need within the art for buffer formulations for pH measurement containing adequate biocide to inhibit microbial growth, while also being capable of withstanding the rigors of sterilization without affecting pH.

DESCRIPTION OF THE INVENTION

Buffer formulations of the present invention are storage stable formulations suitable for sterilization without appreciably altering the pH, and without producing substantial quantities of $CO_2$, or precipitates.

Sterilization of pharmaceutically acceptable formulations can be performed by radiation. Sterilization by radiation can employ either electromagnetic radiation or particulate radiation. See Alfonso R. Gennaro, ed., REMINGTON'S PHARMACEUTICAL SCIENCES, $17^{th}$ Ed., p. 1449 (1985). Electromagnetic radiation is the preferred form of radiation for sterilization of the instant formulations, and gamma radiation is particularly preferred.

In a preferred embodiment, sterilization is performed by use of a gamma irradiation system having a Cobalt-60 source. The system used in the examples and data presented below is a dual source (i.e. two source racks), affording continuous irradiation and wet storage. The sterilization range was 25–35 kGy, set by adjusting the time of exposure to a constant radiation source. All sterilization dose ranges were confirmed by dosimeters.

The buffer formulations of the present invention comprise benzethonium chloride as a biocide. The buffering agent can be a phosphate (e.g., potassium phosphate and/or sodium phosphate). Other common pH electrode calibration buffers suitable for the storage stable buffer formulations of the instant invention are potassium acid phthalate (pH 4); sodium carbonate/sodium bicarbonate (pH 10); 2-[N-Cyclohexylamino]ethanesulfonic acid (CHES, pH range 8.6–10.0); and N-[2-Hydroxyethyl]piperazine-N'-[2-ethanesulfonic acid] (HEPES, pH range 6.8–8.2).

Among other things, we have discovered that benzethonium chloride can be used at a concentration sufficient to impart the desired biocidal effect yet withstand the rigors of gamma sterilization without unduly acidifying the resultant buffer, or otherwise contributing to a deterioration of the properties or appearance of the formulation. Cf. Table 3. We examined a variety of preservatives for use in this buffer. While all were effective biocides pre-sterilization, many did not withstand a gamma sterilization cycle without negatively affecting the buffer integrity. See Table 3. Benzethonium chloride had minimal effect on the final buffer formulation with regard to pH level, stability, and cosmetic factors.

Sterilization by gamma irradiation of buffer formulations containing preservatives can cause acidification of the buffer. This is so even in the case of the benzethonium chloride preservative, although to a much lesser extent than in many other cases. Even the fairly minor acidification induced by benzethonium chloride can be diminished or eliminated. In the case of a phosphate buffer, substantial advantages are achieved when the phosphate concentration is higher than the phosphate concentration used in conventional buffers for calibrating pH electrodes. The higher level of buffering capacity dampens or effectively eliminates acidification from sterilization byproducts, and allows for consistent and predictable post-sterilization pH levels.

Preferably, the buffer is present at a concentration of at least about 50 mM; and still more preferably about 100 mM.

The concentration of benzethonium chloride in the buffer formulations of the present invention is preferably less than 0.01%, still more preferably less than about 0.005%, and most preferably about 0.003%.

In certain applications, this product will be used on mammalian tissue or to measure interstitial pH within mammalian tissue. Thus, in certain applications, it is preferred that the formulation is isoosmotic with the tissue being monitored. Preferred formulations are rendered isoosmotic with human tissue by the addition of NaCl.

A preferred buffer formulation of the present invention is a 100 mM phosphate buffer (using anhydrous $KH_2PO_4$ and $Na_2HPO_4$), adjusted to approximately 300 mosm with NaCl, and with 0.0033% benzethonium chloride as a preservative. Tables 1 and 2 describe the ingredients for two of the preferred embodiments of such calibration buffers.

TABLE 1

Calibration Buffer 1 Formulation

| Constituents | Amount Added (grams) |
| --- | --- |
| $KH_2PO_4$ | 2.722 |
| $Na_2HPO_4$ | 11.357 |
| NaCl (high purity) | 2.922 |
| Benzethonium Chloride | 0.033 |
| Sterile $H_2O$ for Irrigation, USP | 992.966 |

TABLE 2

Calibration Buffer 2 Formulation

| Constituents | Amount Added (grams) |
| --- | --- |
| $KH_2PO_4$ | 10.206 |
| $Na_2HPO_4$ | 3.549 |
| NaCl (high purity) | 2.922 |
| Benzethonium Chloride | 0.033 |
| Sterile $H_2O$ for Irrigation, USP | 991.889 |

Potassium dihydrogenphosphate, $KH_2PO_4$, and sodium phosphate dibasic anhydrous, $Na_2HPO_4$ must be dried prior to use and stored in an oven at 110° and 120° C., respectively. All chemicals should be of reagent grade or of 99%+ purity, with the exception of the benzethonium chloride, which is available at 97% purity. Aseptic technique is highly recommended when mixing buffers. Buffer pH measurements should be done at least 24 hours after formulating the buffer solution to allow for complete $CO_2$ absorption.

Benzethonium chloride is a quaternary ammonium compound commonly used as a preservative in deodorants, topical anti-infectives, antiseptics, disinfectants, wound powders, and in the anthrax vaccine. Additional information can be found in Jon J. Kabara, ed., COSMETIC AND DRUG PRESERVATION, PRINCIPLES AND PRACTICE, ISBN 0-8247-7104-4; and Seymour S. Block, DISINFECTION, STERILIZATION AND PRESERVATION, ISBN 0-8121-0863-9.

TABLE 3

Effect of gamma sterilization (25–35 kGy) on preservatives.

| Preservative | Result post-gamma sterilization |
| --- | --- |
| Germall II | Strong acidification, evolved $CO_2$ |
| Benzalkonium chloride | Precipitated |
| Benzethonium chloride | Acceptable |
| Chlorohexidine | Precipitated |
| Dowicil 200 | Acidified, drifted |
| Methyl paraben | Acidified |
| Propyl paraben | Precipitated |

Our studies show that the effect of gamma irradiation sterilization is a decrease in buffer pH (acidification), particularly in buffers comprising biocidal preservatives. Because we did not observe this effect in preservative-free buffer solutions, we surmise that the preservative is the likely cause of the acidification. As the buffers are intended to be standard solutions for measuring pH, and for calibrating instruments and equipment for measuring pH, any alteration in pH, whether increase or decrease, must be minimized if not eliminated. Gamma irradiation of the benzethonium chloride-containing buffers produced a minimal decrease in pH. When the Calibration Buffer 1 was sterilized with a 25–35 kGy gamma dose, the Calibration Buffer 1 decreased by only 0.030 pH units; and the Calibration Buffer 2 decreased by only 0.011 pH units.

There are at least two important factors for assessing the suitability of various formulations of the instant invention. First, the buffer must inhibit microbiological growth over the time period between buffer construction and product sterilization. Second, the sterilized buffer must meet all other requirements of the buffer, including stability (especially pH stability), biocompatibility, and cosmetics.

Analysis of the formulations for effectiveness of the benzethonium chloride (Table 4) showed excellent results in unsterile buffer over an eight-week period. Preservative effectiveness testing performed over eight weeks, using six different organisms, showed no counts for five of the organisms, and over a 3 log reduction for the sixth organism.

TABLE 4

Effectivity of benzethonium chloride (0.0033% in 100 mM PBS) on buffers

| | | Counts (CFUs) | | | | |
| --- | --- | --- | --- | --- | --- | --- |
| Buffer | Organism | Inoculated | 7 days | 14 days | 28 days | 8 weeks |
| 1 | Escherichia coli | $5.2 \times 10^4$ | $1.1 \times 10^2$ | $4.4 \times 10^1$ | 0.0 | 0.0 |
| | Pseudomonas aeruginosa | $7.9 \times 10^4$ | $1.7 \times 10^2$ | $3.7 \times 10^1$ | 0.0 | 0.0 |

TABLE 4-continued

Effectivity of benzethonium chloride (0.0033% in 100 mM PBS) on buffers

| | | Counts (CFUs) | | | | |
|---|---|---|---|---|---|---|
| Buffer | Organism | Inoculated | 7 days | 14 days | 28 days | 8 weeks |
| | *Staphylococcus aureus* | $6.7 \times 10^4$ | $1.7 \times 10^2$ | $6.0 \times 10^1$ | $1.6 \times 10^1$ | 0.0 |
| | *Candida albicans* | $1.5 \times 10^5$ | $1.6 \times 10^2$ | $1.6 \times 10^2$ | 0.0 | 0.0 |
| | *Aspergillus niger* | $1.3 \times 10^6$ | $5.8 \times 10^2$ | $2.6 \times 10^1$ | 0.0 | 0.0 |
| | *Burkholderia cepacia* | $6.8 \times 10^4$ | $5.8 \times 10^3$ | $2.0 \times 10^3$ | $2.4 \times 10^2$ | $4.9 \times 10^1$ |
| | *Clostridium sporogenes* | $5.7 \times 10^4$ | $7.3 \times 10^2$ | $3.5 \times 10^1$ | $1.9 \times 10^1$ | 0.0 |
| 2 | *Escherichia coli* | $5.1 \times 10^4$ | $0.9 \times 10^2$ | $3.1 \times 10^1$ | 0.0 | 0.0 |
| | *Pseudomonas aeruginosa* | $7.8 \times 10^4$ | $1.4 \times 10^2$ | $3.0 \times 10^1$ | 0.0 | 0.0 |
| | *Staphylococcus aureus* | $6.1 \times 10^4$ | $1.3 \times 10^2$ | $4.1 \times 10^1$ | 0.0 | 0.0 |
| | *Candida albicans* | $1.3 \times 10^5$ | $1.3 \times 10^2$ | $6.5 \times 10^1$ | 0.0 | 0.0 |
| | *Aspergillus niger* | $8.3 \times 10^5$ | $3.3 \times 10^2$ | $2.1 \times 10^1$ | 0.0 | 0.0 |
| | *Burkholderia cepacia* | $6.5 \times 10^4$ | $2.8 \times 10^2$ | $1.8 \times 10^3$ | $2.0 \times 10^2$ | $3.5 \times 10^1$ |
| | *Colstridium sporogenes* | $5.2 \times 10^4$ | $6.4 \times 10^2$ | $2.0 \times 10^1$ | $1.0 \times 10^1$ | 0.0 |

Table 5 shows that the pH of the buffers upon gamma sterilization (25–35 kGy) changes only minimally. These values are stable over time.

TABLE 5 pH of buffers pre-and post-sterilization

| | pH | Δ | N |
|---|---|---|---|
| Calibration Buffer 1 | | | |
| Pre-sterilization | 7.337 | 0.009 | 10 |
| Post-sterilization | 7.304 | 0.015 | 29 |
| Calibration Buffer 2 | | | |
| Pre-sterilization | 6.257 | 0.012 | 10 |
| Post-sterilization | 6.250 | 0.012 | 29 |

We have also demonstrated that the benzethonium chloride in the KMpH™ Calibration Buffers 1 and 2 is an effective antimicrobial preservative for at least eight weeks. We tested the Buffers according to USP protocol for "Antimicrobial Preservatives Effectiveness" (*United States Pharmacopeia*, Volume XXIV, Microbiological Tests, Section (51) Antimicrobial Effectiveness Testing, pp. 1809–11, Official Jan. 1, 2000). Our results showed log reduction of 1.0–3.4 after one week; 2.4 to no organisms after 4 weeks, and 3.3 to no organisms after 8 weeks. Based on those results, the allowable queue time from the time of buffer mixing to the time of sterilization can be up to about eight weeks.

The above buffers passed biocompatibility tests, and show no cosmetic flaws (no perceptible odor, color, or precipitates).

The buffers of the present invention are preferably formulated under aseptic conditions. The buffers of the present invention prevent microorganism growth for at least about eight weeks after being formulated. The buffers can be sterilized, as by gamma irradiation, almost anytime following formulation and stored in an aseptic container with no appreciable change in pH. That is, the formulations of the present invention do not result in substantial acidification as a result of a sterilizing dose of gamma irradiation. By substantial acidification is meant a decrease in pH of at least about 0.1 pH units.

In preferred embodiments, the buffers of the present invention are formulated such that they result in a decrease in pH of no more than about 0.05 pH units following sterilization by gamma irradiation. Still more preferred is a formulation that produces a decrease in pH of about 0.030 pH units or less upon treatment with a sterilizing dose of gamma irradiation. For purposes of this disclosure, a sterilizing dose of gamma irradiation is about 15–35 kGy. Preferred sterilizing doses are in the range of 25–35 kGy.

Another aspect of the invention is a method for formulating an aseptic, storage-stable, standard buffer solution that is of a known, predictable pH, and free of precipitate. The method produces buffers that can be formulated, sterilized by gamma irradiation, and stored, all without substantially altering the pH of the buffer solution. The method involves the addition of benzethonium chloride to a buffer solution, and sterilizing and storing the buffer solution under aseptic, sterile conditions. In at least one embodiment, the method comprises formulating a buffer solution comprising benzethonium chloride, and subjecting the resultant buffer solution to at least about 25–35 kGy gamma irradiation. The resultant buffer is preferably packaged and sealed under aseptic conditions. The resultant buffer solution differs from the pre-sterilized buffer solution by no more than about 0.05 pH units.

The benzethonium chloride is added to the buffers such that the resultant formulation comprises benzethonium chloride at concentrations less than about 0.01%, and preferably less than about 0.005% (by weight). Most preferred is a buffer formulation comprising about 0.0033% benzethonium chloride (by weight).

Still another aspect of the invention is a method for formulating an aseptic, storage stable buffer formulation of constant and predictable pH. The method involves compounding an aqueous formulation comprising: $KH_2PO_4$; $Na_2HPO_4$; NaCl; benzethonium chloride; and Sterile $H_2O$ for Irrigation, USP; and subjecting said formulation to sterilization by gamma irradiation to produce a sterile, aseptic buffer solution. Preferred formulations are those wherein the buffer comprises about 1 to about 15 g. $KH_2PO_4$; about 1 to about 15 g. $Na_2HPO_4$; about 2 to 5 g. sodium chloride; about 800 to about 1100 g. Sterile $H_2O$ for Irrigation, USP; and less than about 0.005% benzethonium chloride (by weight). Still more preferred formulations are those comprising about 2 to about 4 g. of either of $KH_2PO_4$ or $Na_2HPO_4$; about 9 to about 12 g. of either of $KH_2PO_4$ or $Na_2HPO_4$, whichever is not already added to the formulation; about 2.5 to about 3.5 g. sodium chloride; about 950 to about 1050 g. Sterile $H_2O$ for Irrigation, USP; and about 0.005 to about 0.001% benzethonium chloride (by weight).

It will be understood that the foregoing description is merely illustrative of the present invention. The foregoing description is not intended to define or otherwise delimit the scope of the present invention.

What is claimed is:

1. A buffer formulation consisting essentially of:
   (a) benzethonium chloride;
   (b) a buffering agent selected from the group consisting of sodium phosphate, potassium phosphate, potassium acid phthalate, sodium carbonate, sodium bicarbonate, 2-[N-cyclohexylamino]ethanesulfonic acid, N-[2-hydroxyethyl]piperazine-N'-[2-ethanesulfonic acid], and mixtures thereof;
   (c) sodium chloride; and
   (d) water,
   as a solution that exhibits a decrease in pH of about 0.1 units or less and no perceptible precipitate when subjected to 15–35 kGy gamma irradiation.

2. The formulation of claim 1, wherein the concentration of benzethonium chloride in the formulation is greater than 0% but less than 0.01% (by weight).

3. The formulation of claim 1, wherein the concentration of benzethonium chloride in the formulation is about 0.003% (by weight).

4. The formulation of claim 1, wherein the concentration of buffering agent in the formulation is at least about 50 mM.

5. The formulation of claim 1, wherein the concentration of buffering agent in the formulation is about 100 mM.

6. The formulation of claim 1, wherein the concentration of benzethonium chloride in the formulation is about 0.003% (by weight) and the concentration of the buffering agent in the formulation is about 100 mM.

7. The buffer formulation of claim 1, wherein the gamma irradiation produces a decrease in pH of 0.03 units or less.

8. A buffer formulation consisting essentially of a solution of:
   (a) about 0.003% (by weight) benzethonium chloride;
   (b) a buffering agent selected from the group consisting of sodium phosphate dibasic anhydrous, potassium dihydrogenphosphate, and combinations thereof;
   (c) sodium chloride; and
   (d) water.

9. A buffer formulation consisting of:
   (a) about 1 to about 15 g. potassium dihydrogen phosphate;
   (b) about 1 to about 15 g. sodium phosphate dibasic anhydrous;
   (c) about 2 to about 5 g. sodium chloride;
   (d) about 800 to about 1100 g. water; and
   (e) about 0.005% to about 0.001% (by weight) benzethonium chloride.

10. A method for formulating a sterile, storage stable buffer for calibrating pH electrodes comprising:
    (a) preparing a liquid mixture comprising benzethonium chloride and a buffering agent selected from the group consisting of: sodium phosphate, potassium phosphate, potassium acid phthalate, sodium carbonate, sodium bicarbonate, 2-[N-cyclohexylamino]ethanesulfonic acid, and N-[2-hydroxyethyl]piperazine-N'-[2-ethanesulfonic acid]; and
    (b) subjecting the mixture to sterilization by gamma irradiation.

11. The method of claim 10, wherein the sterilization step consists of subjecting the mixture to 15–35 kGy of gamma irradiation.

12. The method of claim 10, wherein the buffering agent is added to the mixture to a concentration of about 50 mM to about 200 mM.

13. The method of claim 10, wherein the buffering agent is added to the mixture to a concentration of about 50 mM to about 100 mM.

14. The method of claim 10, wherein the benzethonium chloride is added to the mixture to a concentration of about 0.001% to about 0.01% (by weight).

15. The method of claim 10, wherein the gamma irradiation effects a change in pH of the buffer mixture of no more than about 0.05 pH units.

16. A method of calibrating pH electrodes comprising
    (a) formulating a buffer solution of known pH consisting essentially of $KH_2PO_4$, $Na_2HPO_4$, NaCl, water, and benzethonium chloride;
    (b) irradiating the buffer solution with about 15–35 kGy of gamma radiation;
    (c) exposing pH electrodes to be calibrated to the buffer solution;
    (d) detecting the pH as measured by the pH electrodes; and
    (e) comparing the pH detected in step (d) with the known pH of the buffer solution.

17. A buffer formulation consisting essentially of:
    (a) benzethonium chloride;
    (b) a buffering agent selected from the group consisting of sodium phosphate, potassium phosphate, potassium acid phthalate, sodium carbonate, sodium bicarbonate, 2-[N-cyclohexylamino]ethanesulfonic acid, N-[2-hydroxyethyl]piperazine-N'-[2-ethanesulfonic acid], and mixtures thereof;
    (c) sodium chloride; and
    (d) water,
    as a solution that prevents microorganism growth for at least about 8 weeks after being formulated and, when subjected to about 15–35 kGy gamma irradiation exhibits a decrease in pH of about 0.1 pH units or less.

18. The formulation of claim 17, wherein the concentration of benzethonium chloride in the formulation is greater than 0% but less than 0.01% (by weight).

19. The formulation of claim 17, wherein the concentration of buffering agent in the formulation is about 100 mM.

20. The formulation of claim 17, wherein the concentration of benzethonium chloride in the formulation is about 0.003% (by weight) and the concentration of the buffering agent in the formulation is about 100 mM.

* * * * *